US009518897B2

(12) United States Patent
Williamson et al.

(10) Patent No.: US 9,518,897 B2
(45) Date of Patent: Dec. 13, 2016

(54) INTELLIGENT BAG FILLING FOR EXHAUST SAMPLING SYSTEM

(71) Applicant: AVL TEST SYSTEMS, INC., Plymouth, MI (US)

(72) Inventors: James Patrick Williamson, Pinckney, MI (US); William Martin Silvis, Ann Arbor, MI (US)

(73) Assignee: AVL TEST SYSTEMS, INC., Plymouth, MI (US)

( * ) Notice: Subject to any disclaimer, the term of this patent is extended or adjusted under 35 U.S.C. 154(b) by 27 days.

(21) Appl. No.: 14/402,623

(22) PCT Filed: May 28, 2013

(86) PCT No.: PCT/US2013/042871
§ 371 (c)(1),
(2) Date: Nov. 20, 2014

(87) PCT Pub. No.: WO2013/181145
PCT Pub. Date: Dec. 5, 2013

(65) Prior Publication Data
US 2015/0153254 A1      Jun. 4, 2015

Related U.S. Application Data

(60) Provisional application No. 61/791,635, filed on Mar. 15, 2013, provisional application No. 61/652,367, filed on May 29, 2012.

(51) Int. Cl.
*G01N 1/22*     (2006.01)
*G01M 15/10*    (2006.01)
*G01N 33/00*    (2006.01)

(52) U.S. Cl.
CPC ............ *G01N 1/2252* (2013.01); *G01M 15/10* (2013.01); *G01N 33/0018* (2013.01); *G01N 33/0027* (2013.01); *G01N 2001/2255* (2013.01)

(58) Field of Classification Search
CPC ..................... G01N 2001/2255; G01N 1/2252
(Continued)

(56) References Cited

U.S. PATENT DOCUMENTS 3,499,717 A    3/1970   Rosenberg et al.
3,603,155 A    9/1971   Morris et al.
(Continued)

FOREIGN PATENT DOCUMENTS

DE          4017473 A1     11/1991
DE          19604417 C1     9/1997
(Continued)

OTHER PUBLICATIONS

Nevius et al., "Improved PHEV Emission Measurements in a Chassis Dynamometer Test Cell," SAE International J. Engines, vol. 3, Issue 1, Apr. 12, 2010, pp. 1113-1123.
(Continued)

*Primary Examiner* — Michael A Lyons
*Assistant Examiner* — Jean Morello
(74) *Attorney, Agent, or Firm* — Harness, Dickey & Pierce, P.L.C.

(57) ABSTRACT

An exhaust sampling system for an engine is provided. The exhaust sampling system may include a source of exhaust gas, an exhaust collection unit including at least one collection bag that selectively receives the exhaust gas, and a first sample probe in fluid communication with the source of exhaust gas that selectively supplies the at least one collection bag with the exhaust gas at an extraction rate. The exhaust sampling system may also include a controller that permits flow of the exhaust gas from the first sample probe to the at least one collection bag in a first state and prevents (Continued)

flow of the exhaust gas from the first sample probe to the at least one collection bag in a second state. The controller may control the extraction rate of the first sample probe based on a time during a test phase at which the engine is switched to an ON state.

30 Claims, 5 Drawing Sheets

(58) Field of Classification Search
USPC .................................................. 73/23.31, 864
See application file for complete search history.

(56) References Cited

U.S. PATENT DOCUMENTS

| | | | |
|---|---|---|---|
| 3,610,047 | A | 10/1971 | List et al. |
| 3,699,814 | A | 10/1972 | Kaufman |
| 3,793,887 | A | 2/1974 | Anderson et al. |
| 4,022,059 | A * | 5/1977 | Schontzler ............... G01N 1/18 |
| | | | 141/130 |
| 4,040,783 | A | 8/1977 | Collin |
| 5,058,440 | A | 10/1991 | Graze, Jr. |
| 5,195,318 | A | 3/1993 | Shinzawa et al. |
| 5,453,124 | A | 9/1995 | Moslehi et al. |
| 5,456,124 | A | 10/1995 | Colvin |
| 5,546,788 | A | 8/1996 | Dickow |
| 5,650,565 | A | 7/1997 | Nagy et al. |
| 5,821,435 | A | 10/1998 | Kojima |
| 6,016,711 | A | 1/2000 | Ullman et al. |
| 6,134,942 | A | 10/2000 | Pasquereau et al. |
| 6,282,944 | B1 | 9/2001 | Bornemann |
| 6,370,936 | B1 | 4/2002 | Yamagishi et al. |
| 6,405,577 | B2 | 6/2002 | Hanashiro et al. |
| 6,412,333 | B2 | 7/2002 | Inoue et al. |
| 6,443,021 | B2 | 9/2002 | Hanashiro et al. |
| 6,470,732 | B1 | 10/2002 | Breton |
| 6,490,937 | B2 | 12/2002 | Hanashiro et al. |
| 6,497,156 | B2 | 12/2002 | Dagefoerde |
| 6,578,440 | B2 | 6/2003 | Lewis |
| 6,962,090 | B2 | 11/2005 | McDonald et al. |
| 7,071,002 | B1 | 7/2006 | Tefft et al. |
| 7,559,262 | B2 | 7/2009 | Silvis et al. |
| 7,621,170 | B2 * | 11/2009 | Hoffmann ............ G01M 3/2876 |
| | | | 73/1.72 |
| 8,181,543 | B2 | 5/2012 | Silvis et al. |
| 8,272,248 | B2 | 9/2012 | Guenther et al. |
| 9,243,983 | B2 | 1/2016 | Guenther et al. |
| 2001/0003915 | A1 | 6/2001 | Inoue et al. |
| 2001/0013245 | A1 | 8/2001 | Hanashiro et al. |
| 2003/0093943 | A1 | 5/2003 | Jordan |
| 2003/0149536 | A1 | 8/2003 | Silvis et al. |
| 2004/0139785 | A1 | 7/2004 | Abdul-Khalek |
| 2004/0200265 | A1 | 10/2004 | Eden et al. |
| 2004/0226354 | A1 | 11/2004 | Schmidt |
| 2005/0056103 | A1 | 3/2005 | Hirai et al. |
| 2005/0109128 | A1 | 5/2005 | Pasquereau et al. |
| 2005/0160838 | A1 | 7/2005 | Weaver |
| 2005/0236040 | A1 | 10/2005 | Farthing et al. |
| 2006/0243026 | A1 | 11/2006 | Graze et al. |
| 2010/0000339 | A1 | 1/2010 | Silvis et al. |
| 2010/0024417 | A1 | 2/2010 | Pierpont et al. |
| 2011/0146378 | A1 | 6/2011 | Brand et al. |
| 2011/0252864 | A1 | 10/2011 | Guenther et al. |
| 2012/0304737 | A1 | 12/2012 | Guenther et al. |

FOREIGN PATENT DOCUMENTS

| | | |
|---|---|---|
| EP | 42800 A1 | 12/1981 |
| EP | 610523 A1 | 8/1994 |
| EP | 928962 A1 | 7/1999 |
| EP | 973080 A2 | 1/2000 |
| EP | 1333270 A1 | 8/2003 |
| EP | 2469259 A1 | 6/2012 |
| JP | 07-035660 | 2/1995 |
| JP | H08226879 A | 9/1996 |
| JP | H10-318810 A | 12/1998 |
| JP | H11108809 A | 4/1999 |
| JP | H11-344425 A | 12/1999 |
| JP | 2000180315 A | 6/2000 |
| JP | 2000292321 A | 10/2000 |
| JP | 2001004504 A | 1/2001 |
| JP | 2005055333 A | 3/2005 |
| JP | 2006105024 A | 4/2006 |
| WO | 0014506 A1 | 3/2000 |
| WO | 0190741 A2 | 11/2001 |
| WO | 2013181145 A1 | 12/2013 |

OTHER PUBLICATIONS

Hood et al., "Predicting and Preventing Water Condensation in Sampled Vehicle Exhaust for Optimal CVS Dilution," SAE Technical Paper 980404, 1998, doi:10.4271/980404.
e-CFR Title 40, Part 1065, Engine-Testing Procedures, 164 pages.
e-CFR Title 40, Part 1066, Vehicle-Testing Procedures, 73 pages.
Emission Standards Reference Guide, EPA Federal Test Procedure (FTP).
e-CFR §1066.815 Exhaust emission test procedures for FTP testing.
International Search Report and Written Opinion of the International Searching Authority for PCT/US2013/042871, mailed Sep. 5, 2013; ISA/KR.
Extended European Search Report and Written Opinion for PCT/US2013/04287, mailed Jan. 21, 2016.
Edkins, Jo; Mean, median, mode; 2006; Numbers Index, http://gwydir.demon.co.uk!jo/numbers/pictogram/box.htm, pp. 1-3.
Chinese Office Action for Application No. 201380028461.3 dated Nov. 30, 2015.
Baumann, Philipp, et al., "Investigation of the Influencing Parameters Using Optimized Exhaust Emissions Measurement Systems with Different Modern Plug-in Hybrid Electrical Vehicles," SAE Technical Paper 2015-01-1069, 2015.
Chinese Office Action for Application No. 201380028461.3 dated Jul. 5, 2016.
Extended European Search Report for Application No. 13168604.0 dated Jul. 26, 2016.

* cited by examiner

INTELLIGENT BAG FILLING FOR EXHAUST SAMPLING SYSTEM

CROSS-REFERENCE TO RELATED APPLICATIONS

This application claims the benefit of U.S. Provisional Application No. 61/791,635, filed on Mar. 15, 2013 and claims the benefit of U.S. Provisional Application No. 61/652,367, filed on May 29, 2012. The entire disclosures of each of the above applications are incorporated herein by reference.

FIELD

The present disclosure relates to an exhaust sampling system.

BACKGROUND

This section provides background information related to the present disclosure which is not necessarily prior art.

Exhaust sampling systems are conventionally used in conjunction with engines or vehicles with internal combustion engines to determine the mass of pollutants produced by the engine during use. Such exhaust sampling systems may include a constant volume sampler (CVS) or a bag mini-diluter (BMD) that extract diluted exhaust gas for analysis in an effort to determine the pollutant mass of the particular engine.

During operation of a CVS system, for example, engine exhaust is diluted with a diluent gas, and a sample of the diluted exhaust is proportionally extracted and stored in one or more sample bags. Depending on the engine or vehicle size, drive or duty cycle, and ambient conditions, the CVS total flow rate, which includes both the diluent gas and engine exhaust, is selected to ensure the diluted exhaust sample does not condense water when extracted during sampling, stored in the bags, or analyzed after the test phase. Once the sample bags are filled with diluted exhaust gas, the contents of the sample bags may be analyzed to determine the pollutant mass over the test phase for the particular engine.

Vehicles incorporating traditional combustion engine powertrains continuously operate an internal combustion engine of the powertrain and, as a result, an internal combustion engine associated with a conventional vehicle powertrain is continuously operated during a test phase. As a result, collection of the diluted exhaust by the CVS system is likewise continuous throughout the test phase.

New powertrains are being developed, however, that intermittently use an internal combustion engine during operation of a vehicle. For example, a hybrid-electric vehicle may only use an internal combustion engine when recharging a battery of the vehicle. Such powertrains pose challenges for both CVS sampling systems and BMD sampling systems, as each system is conventionally configured to sample (i.e., collect) for analysis a diluted exhaust gas from an internal combustion engine that operates during an entire sample phase.

SUMMARY

This section provides a general summary of the disclosure, and is not a comprehensive disclosure of its full scope or all of its features.

An exhaust sampling system for an engine is provided. The exhaust sampling system may include a source of exhaust gas, an exhaust collection unit including at least one collection bag that selectively receives the exhaust gas, and a first sample probe in fluid communication with the source of exhaust gas that selectively supplies the at least one collection bag with the exhaust gas at an extraction rate. The exhaust sampling system may also include a controller that permits flow of the exhaust gas from the first sample probe to the at least one collection bag in a first state and prevents or bypasses flow of the exhaust gas from the first sample probe to the at least one collection bag in a second state. The controller may control the extraction rate of the first sample probe based on a time during a test phase at which the engine is switched to an ON state.

In another configuration, an exhaust sampling system for an engine or vehicle is provided. The exhaust sampling system may include a dilution tunnel in which exhaust gas from the engine is diluted with a first diluent gas, an exhaust collection unit including at least one collection bag that selectively receives the diluted exhaust gas, and a first sample probe in fluid communication with the dilution tunnel and operable to selectively supply the at least one collection bag with a portion of the diluted exhaust gas during a test phase. The exhaust sampling system may also include a controller that permits flow of the diluted exhaust gas from the first sample probe to the at least one collection bag in a first state and prevents or bypasses flow of the diluted exhaust gas from the first sample probe to the at least one collection bag in a second state. The controller may selectively supply a second diluent gas to the at least one collection bag during the test phase and selectively prevent flow of the second diluent gas to the at least one collection bag during the test phase.

In yet another configuration, an exhaust sampling system for an engine or vehicle is provided. The exhaust sampling system may include a source of exhaust gas, an exhaust collection unit including at least one collection bag that selectively receives the exhaust gas, a first sample probe in fluid communication with the source of exhaust gas and operable to selectively supply the at least one collection bag with the exhaust gas during a test phase, and a source of fill gas. The exhaust sampling system may also include a first flow path in fluid communication with the first sample probe and the exhaust collection unit, and a second flow path in fluid communication with the source of fill gas and the exhaust collection unit. The exhaust sampling system may also include a controller that permits flow of the exhaust gas from the first sample probe to the at least one collection bag in a first state and prevents or bypasses flow of the exhaust gas from the first sample probe to the at least one collection bag in a second state. The controller may supply exhaust gas to the at least one collection bag through the first flow path during the test phase and supply the fill gas to the at least one collection bag through the second flow path during the test phase.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
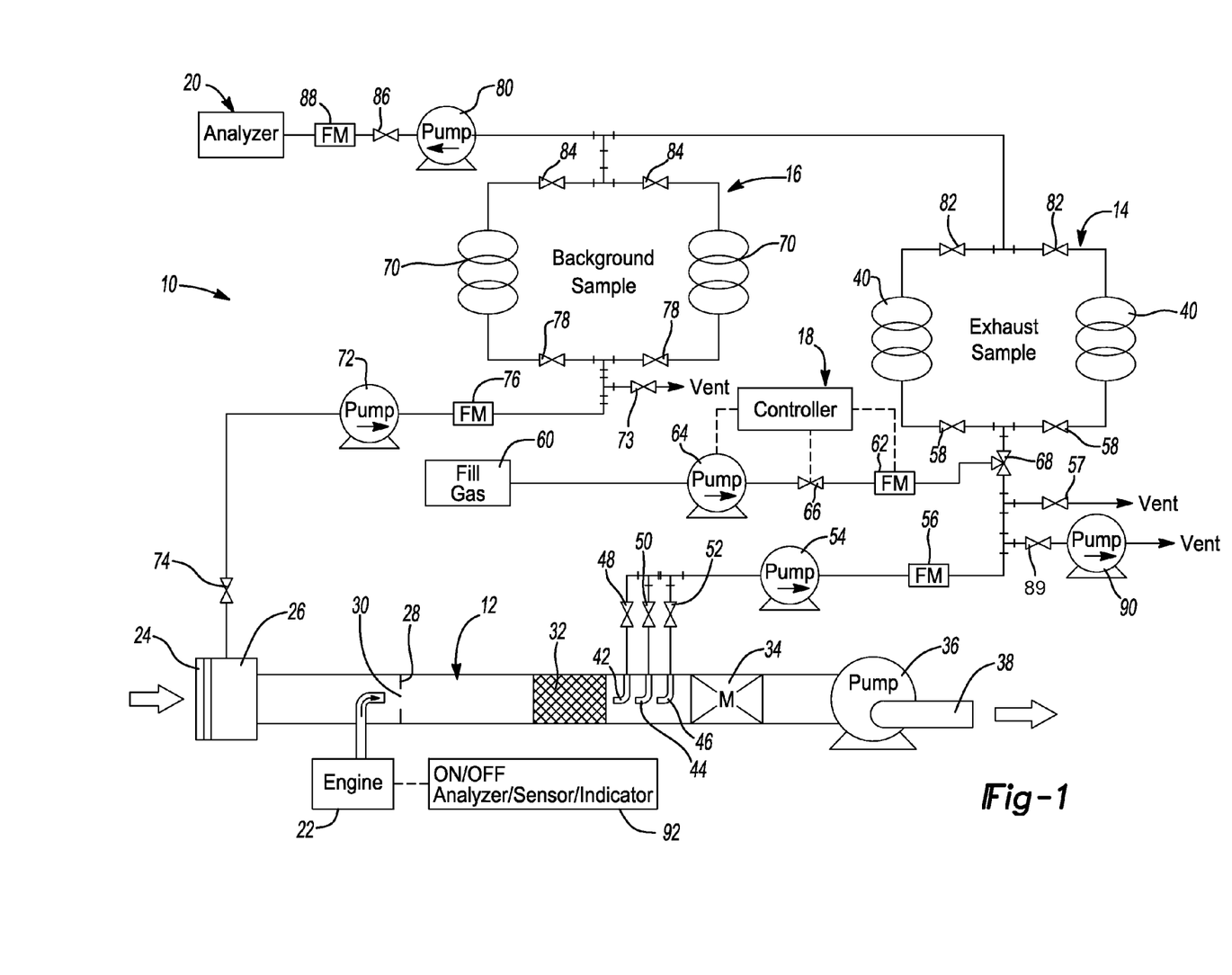
FIG. 1 is a schematic view of a CVS sampling system in accordance with the principles of the present disclosure.

With reference to FIG. 1, an exhaust sampling system 10 is provided and may include a dilution tunnel 12, an exhaust collection unit 14, a background collection unit 16, a controller 18, and one or more analyzers 20. As will be described in greater detail below, the exhaust collection unit 14 collects diluted exhaust gas from the dilution tunnel 12 and provides a sample of the diluted exhaust gas to the analyzers 20 to allow the analyzers 20 to determine a concentration of pollutants in the diluted exhaust gas sample.

The dilution tunnel 12 may be fluidly coupled to an engine 22 and may receive a stream of exhaust gas from the engine 22. In one configuration, the engine (22) is an internal combustion engine (ICE) configured for use in a vehicle having an electrically driven powertrain (neither shown). The dilution tunnel 12 may also be fluidly coupled to a diluent gas inlet 24 that provides diluent gas to the dilution tunnel 12. As known in the art, the diluent gas provided to the dilution tunnel 12 at the diluent gas inlet 24 may be ambient air. The diluent gas inlet 24 may include a filter 26 that removes impurities from the air stream prior to the air stream entering the dilution tunnel 12.

A mixing plate 28 may be disposed within the dilution tunnel 12 and may include an opening or aperture 30 formed therethrough. The aperture 30 may cooperate with a body of the mixing plate 28 to cause air entering the dilution tunnel 12 at the inlet 24 to be mixed, as the air flows through the aperture 30 of the mixing plate 28. Accordingly, exhaust gas from the engine 22 mixes with diluent gas received by the dilution tunnel 12 at the diluent gas inlet 24 such that a substantially homogeneous mixture of diluent gas and exhaust gas is received by a heat exchanger 32, which may be disposed downstream of the mixing plate 28.

The heat exchanger 32 may be located along a length of the dilution tunnel 12 and may be used to maintain the mixture of exhaust gas and diluent gas at a desired temperature. The temperature of the mixture may be determined by a temperature sensor or other measuring device 34 disposed downstream of the heat exchanger 32.

A pump 36 may be fluidly coupled to the dilution tunnel 12 at an opposite end of the dilution tunnel 12 than the diluent gas inlet 24. The pump 36 may impart a fluid force on the dilution tunnel 12 to draw air into the diluent gas inlet 24 and through the filter 26. The force imparted on the diluent gas inlet 24 causes diluent gas to enter the dilution tunnel 12 and mix with exhaust gas from the engine 22. Specifically, the force imparted on the diluent gas and on the exhaust gas from the engine 22 causes the exhaust gas and the diluent gas to encounter the mixing plate 28 and flow through the aperture 30. In so doing, the diluent gas and the exhaust gas are mixed. Accordingly, a substantially homogeneous mixture is received by the heat exchanger 32 and by the temperature sensor 34. The homogeneous mixture of diluent gas and exhaust gas may then be expelled from the dilution tunnel 12 via an outlet 38 of the pump 36.

With continued reference to FIG. 1, the exhaust collection unit 14 may be fluidly coupled to the dilution tunnel 12 to receive a portion of the diluted exhaust gas (i.e., the homogeneous mixture of diluent gas and exhaust gas) disposed within and flowing through the dilution tunnel 12. The exhaust collection unit 14 may receive and store a portion of the diluted exhaust gas prior to the diluted exhaust gas being analyzed by the analyzers 20.

The exhaust collection unit 14 may include one or more sample bags 40 that store the diluted exhaust gas therein. The sample bags 40 may be fluidly coupled to one or more sample probes that are in fluid communication with the dilution tunnel 12. As shown in FIG. 1, the sample probes may include a first sample probe 42, a second sample probe 44, and a third sample probe 46. The sample probes 42, 44, 46 may be identical such that the nozzles (not labeled) of each sample probe 42, 44, 46 that receive the flow of diluted exhaust gas from within the dilution tunnel 12 are substantially equal. In other words, the nozzles include substantially the same diameter such that the rate of flow received by each sample probe 42, 44, 46 is substantially identical. Conversely, the sample probes 42, 44, 46 may include different nozzles such that an inner diameter of each sample probe 42, 44, 46 is different, thereby providing each sample probe 42, 44, 46 with a different sample extraction rate. Finally, while the sample probes 42, 44, 46 may include different diameters and, thus, different extraction rates, two of the sample probes 42, 44, 46 may include the same diameter and, thus, the same extraction rate while the other of the three sample probes 42, 44, 46 includes a different diameter and, thus, a different extraction rate. Regardless of the particular construction of the various sample probes 42, 44, 46, the sample probes 42, 44, 46 extract a sample of the diluted exhaust gas from the dilution tunnel 12 and communicate the extracted sample of diluted exhaust gas to the sample bags 40 for storage.

Each of the sample probes 42, 44, 46 may be associated with a control valve that controls the flow of diluted exhaust gas from the sample probes 42, 44, 46 to the sample bags 40. Namely, the first sample probe 42 may be fluidly coupled to a first control valve 48; the second sample probe 44 may be fluidly coupled to a second control valve 50; and the third sample probe 46 may be fluidly coupled to a third control valve 52. The control valves 48, 50, 52 control the flow of diluted exhaust gas respectively received by the sample probes 42, 44, 46 to the sample bags 40. The control valves 48, 50, 52 may be solenoid-actuated valves, for example, that are movable between an open state and a closed state. Alternatively, one or more of the control valves 48, 50, 52 may be stepper valves that are incrementally movable from a fully open state to a closed state. In other words, one or more of the control valves 48, 50, 52 are variable valves having any number of open states between the fully open state and the fully closed state to provide a degree of adjustability to one or more of the valves 48, 50, 52. Accordingly, if one or more of the control valves 48, 50, 52 includes a stepper valve, the control valves 48, 50, 52 may meter the flow of diluted exhaust gas from the dilution tunnel 12 to the sample bags 40 to finely control the extraction rate of the diluted exhaust gas and, ultimately, the amount of diluted exhaust gas received by the sample bags 40 during a test interval or test phase.

Diluted exhaust gas may be received by the sample probes 42, 44, 46 and may be drawn through the control valves 48, 50, 52 by a pump 54. Specifically, the pump 54 may be disposed downstream of the control valves 48, 50, 52 and may impart a force on the sample probes 42, 44, 46 to cause diluted exhaust gas to be drawn into the sample probes 42, 44, 46 and to flow through the control valves 48, 50, 52.

The diluted exhaust gas drawn through the control valves 48, 50, 52 may also flow through a flow meter 56 prior to being received by the sample bag 40. The diluted exhaust gas may be received by one or more of the sample bags 40, whereby flow of the diluted exhaust gas into the respective sample bags 40 is controlled by a control valve 58 disposed upstream of each of the sample bags 40. As indicated above, the sample probes 42, 44, 46 may be replaced with a single sample probe, and the control valves 48, 50, 52 may be replaced with a single control valve. For example, the control valves 48, 50, 52 may be replaced with a flow control device such as a mass flow controller which, as known in the art, includes a control valve and a flow meter. Since the mass flow controller includes a flow meter, the flow meter 56 may be omitted in these implementations.

While the sample bags 40 are described and shown as receiving diluted exhaust gas from the dilution tunnel 12 via the sample probes 42, 44, 46 and control valves 48, 50, 52, the sample bags 40 may additionally receive fill gas 60 at any point during a test interval or test phase. The fill gas 60 may be drawn through a flow meter 62 by a pump 64 prior to being received by the sample bags 40. The fill gas 60 may flow through a control valve 66 prior to reaching the flow meter 62 and may flow through a control valve 68 prior to being received by the sample bags 40. The control valve 66 may be selectively moved between an open state permitting flow of fill gas 60 to the flow meter 62 and a closed state preventing flow of fill gas 60 to the flow meter 62. The fill gas 60 is permitted to enter the sample bags 40 when the control valve 68 is an open state and is prevented from entering the sample bags 40 when the control valve 68 is in a closed state.

As shown in FIG. 1, the controller 18 may be in communication with the flow meter 62, the pump 64, and the control valve 66 to control the amount of fill gas 60 supplied to the sample bags 40 during a test interval or test phase. For example, if the amount of diluted exhaust gas received by the sample bags 40 during a test interval or test phase is insufficient to allow the analyzers 20 to determine the pollutant mass contained within the exhaust gas, the controller 18 may energize the pump 64 and may open the control valve 66 to supply the sample bags 40 with a volume of fill gas 60. The fill gas 60 mixes with the diluted exhaust gas disposed within the sample bags 40 and serves to supplement the volume disposed within each sample bag 40. Further, the fill gas 60 may be a clean, dry gas that reduces the likelihood of condensation forming within the sample bags 40. Additionally or alternatively, the fill gas 60 may be the diluent gas provided to the dilution tunnel 12 at the diluent gas inlet 24.

The background collection unit 16 may be used by the analyzers 20 when determining the pollutant mass contained within the diluted exhaust gas provided by the exhaust collection unit 14. Specifically, the analyzers 20 may analyze a sample of the diluent gas provided to the dilution tunnel 12 at the diluent gas inlet 24 to allow the analyzers 20 to account for any background contaminates within the diluent gas supplied at the diluent gas inlet 24.

The background collection unit 16 may include one or more sample bags 70, a pump 72, and a flow control device such as a control valve 74. The pump 72 may draw diluent gas from the filter 26 through the control valve 74 when the control valve 74 is in an open state. The diluent gas drawn from the filter 26 by the pump 72 may be directed through a flow meter 76 prior to being received by the sample bags 70. The diluent gas may flow through the flow meter 76 and may be received by the sample bags 70 for collection. The sample bags 70 may be respectively associated with control valves 78 that selectively permit the flow of diluent gas into one or more of the sample bags 70.

With continued reference to FIG. 1, the analyzers 20 is shown as being fluidly coupled to the exhaust collection unit 14 and as being fluidly coupled to the background collection unit 16. Accordingly, the analyzers 20 may receive a diluted exhaust gas sample from the exhaust collection unit 14 and may receive a diluent gas sample from the background collection unit 16.

The analyzers 20 may receive a sample of diluted exhaust gas from the exhaust collection unit 14 and/or may receive a sample of diluent gas from the background collection unit 16 by imparting a force on the fluid contained within the units 14, 16 via a pump 80. The pump 80 may draw diluted exhaust gas from the exhaust collection unit 14 when one or more control valves 82 associated with the exhaust collection unit 14 are in an open state. Likewise, the pump 80 may draw diluent gas from the background collection unit 16 when one or more control valves 84 associated with the background collection unit 16 are in an open state. The diluted exhaust gas sample or diluent gas sample may be drawn from the respective units 14, 16 and may flow through a control valve 86 and flow meter 88 prior to reaching the analyzers 20. Once the analyzers 20 receive the diluted exhaust gas sample from the exhaust collection unit 14 and/or the diluent gas sample from the background collection unit 16, the analyzers 20 may determine the pollutant mass contained within the diluted exhaust gas sample.

With continued reference to FIG. 1, operation of the exhaust sampling system 10 will be described in detail. The following operation of the exhaust sampling system 10 may be performed by the controller 18. While not specifically illustrated in FIG. 1, the controller 18 may be in communication with the temperature sensor 34, the pumps 36, 54, 64, 72, 80, the control valves 48, 50, 52, 58, 66, 68, 74, 82, 84, 86, and the flow meters 56, 62, 76. Accordingly, the controller 18 may receive operating data from the temperature sensor 34 and from the flow meters 56, 62, 76, and may use the foregoing information to control the pumps 36, 54, 64, 72, 80 and the control valves 48, 50, 52, 58, 66, 68, 74, 82, 84, 86 in an effort to allow the analyzers 20 to obtain an accurate reading of the pollutant mass contained within the diluted exhaust gas disposed within the dilution tunnel 12.

The controller 18 may be programmed to run any number of test procedures having any number of test intervals or test phases. For example, the controller 18 may sample diluted exhaust gas from the dilution tunnel 12 during a test phase of five hundred and five seconds (505 s) by controlling the various pumps 36, 54, 64, 72, 80 and control valves 48, 50, 52, 58, 66, 68, 74, 82, 84, 86. A test phase is that portion of a test procedure during which exhaust gas is collected in one or more of the sample bags 40. A test procedure may include multiple test phases, and exhaust gas may be collected in a different one of the sample bags 40 during each one of the test phases. For example, the U.S. Environmental Protection Agency Federal Test Procedure (40 CFR 1066.815) includes a cold transient phase, a cold stabilized phase, a hot transient phase, and a hot stabilized phase, and exhaust gas is collected in different sample bags during each of these four test phases. Thus, in exhaust sample systems that add fill gas prior to or following a test phase, fill gas may be added to one sample bag during a test phase in which exhaust gas is collected in another sample bag. However, discussions herein regarding adding diluent gas and/or fill gas to a sample bag "during a test phase" refer exclusively herein, as well as in the claims, to adding diluent gas and/or fill gas to a sample bag during the same test phase in which exhaust gas is collected in that sample bag. While any number of test procedures may be performed including test phases having virtually any length, the following description will be made with reference to an exemplary test phase having a length of five hundred and five seconds (505 s).

The controller 18 may initiate a test phase at a zero time. If at the zero time the engine 22 is not running, the controller 18 may move the valves 48, 50, 52 into the open state and may energize the pump 54 to vent the diluent gas drawn from the dilution tunnel 12. Specifically, the controller 18 may open a valve 57 downstream of the pump 54 to vent the diluent gas drawn from the dilution tunnel 12 when the engine 22 is in the OFF state. The controller 18 may also ensure that the sample bags 40 are completely empty by opening a valve 89 and energizing a pump 90 that may be used to evacuate any air disposed within the sample bags 40 prior to initiation of the test phase.

The controller 18 may maintain the pump 54 in the energized state and the valves 48, 50, 52 in the open state while the engine 22 is in the OFF state. The controller 18 may likewise maintain the pump 72 in the energized state and the valve 74 in the open state when the engine 22 is in the OFF state. As with the diluent gas extracted from the dilution tunnel 12 by the sample probes 42, 44, 46 when the engine 22 is in the OFF state, the diluent gas extracted by the pump 72 when the engine 22 is in the OFF state may be vented by opening a valve 73 disposed downstream from the pump 72.

The controller 18 may be in communication with a sensor 92 that monitors operation of the engine 22. Additionally or alternatively, the controller 18 may receive the state of the engine 22 (i.e., ON or OFF) from another system such as a computer or controller that controls the test cycle (i.e., a test-automation system) or from a CAN bus or OBD (on-board data) of a vehicle under test. For example, as known in the art, the controller 18 may determine the state of the engine 22 based on a flow rate of exhaust gas flowing through a tailpipe of the engine 22, a pressure of exhaust gas flowing through the tailpipe, and a change in pressure of diluted exhaust gas flowing through the dilution tunnel 12. Regardless of how the controller 18 determines the state of the engine 22, the controller 18 may maintain the valves 57, 73 in the open state until the controller 18 receives a signal from the sensor 92 that the engine 22 is in the ON state. At this point, the controller 18 may close the valves 57, 73 to prevent venting of the diluent gas extracted from the dilution tunnel 12. The engine 22 is in the ON state anytime the engine 22 produces exhaust gas, which may include periods when the engine 22 is cranking, the engine 22 is running, and/or a brief (e.g., 5 second) period after the engine 22 stops running.

The controller 18 may record the time—during the test interval or test phase—at which the engine 22 turns ON, as reported by the sensor 92. Namely, the controller 18 may determine the time from the zero time recorded at the beginning of the test phase to determine how much time has elapsed during the test phase prior to the engine turning ON. The controller 18 may record and utilize the ON time of the engine 22 to ensure a sufficient volume is collected by the sample bags 40 at a desired dilution ratio, as will be discussed in greater detail below.

The controller 18 may determine the sample flow rate for the sample bags 40 based on the size of the sample bags 40. Namely, the controller 18 may determine the sample flow rate that would be required to fill the sample bags 40 if the engine 22 is running during the entire test phase. The sample fill flow rate may be determined by the length of the collection period (i.e., five hundred and five seconds in the present example) and the volume of the sample bags 40. The sample fill flow rate may be determined by dividing the volume of the sample bags 40 (i.e., the max target fill volume) by the length of the test phase (five hundred and five seconds).

As thus far described, the controller 18 only closes the valves 57, 73 when the engine 22 is moved into the ON state, as indicated by the sensor 92. When the engine 22 is not running (i.e., is in an OFF state), the valves 57, 73 are in the open state to vent diluent gas collected from the dilution tunnel 12. Accordingly, when the engine 22 is in the OFF state and the valves 57, 73 are in the open state, the exhaust collection unit 14 and the background collection unit 16 do not collect a sample within the respective sample bags 40, 70.

If the engine 22 is in the ON state for the entire test phase, the controller 18 may simultaneously energize the pumps 54, 72 and open the valves 48, 50, 52, 74 to allow the sample bags 40 of the exhaust collection unit 14 and the sample bags 70 of the background collection unit 16 to respectively collect a diluted exhaust gas sample and a diluent gas sample. The pumps 54, 72 will remain energized and the valves 48, 50, 52, 74 will remain open—provided the engine 22 remains in the ON state.

When the sensor 92 indicates that the engine 22 is in the ON state, the controller 18 determines the flow rate required to allow the sample bags 40 of the exhaust collection unit 14 and the sample bags 70 of the background collection unit 16 to receive a sufficient volume of diluted exhaust gas and diluent gas, respectively. Alternatively, the controller 18 can continuously calculate and adjust the flow rate until the sensor 92 indicates that the engine 22 is in the ON state.

In order to allow the analyzers 20 to analyze the diluted exhaust gas sample received from the exhaust collection unit 14 and to analyze the diluent gas sample received from the background collection unit 16, the sample bags 40 of the exhaust collection unit 14 must receive a sufficient volume of diluted exhaust gas and the sample bags 70 of the background collection unit 16 must receive a sufficient volume of diluent gas. The volume of diluted exhaust gas received by the sample bags 40 of the exhaust collection unit 14 is determined based on the extraction rate of diluted exhaust gas from the dilution tunnel 12 by the sample probes 42, 44, 46. Because the controller 18 only opens the valves 58 to collect diluted exhaust gas from the dilution tunnel 12 when the engine 22 is in the ON state, an insufficient volume of diluted exhaust gas may be collected if the engine 22 is only in the ON state for a short time during the five hundred and five second (505 s) test phase.

The controller 18 ensures that sampling of the diluted exhaust gas from the dilution tunnel 12 achieves the minimum volume required by the analyzers 20—regardless of the state of the engine 22 (i.e., ON or OFF). In short, the controller 18 maintains the valves 58, 78 in the closed state and the bypass valves 57, 73 in the open state until a point in time during the test phase in which the valves 58, 78 must be opened and the bypass valves 57, 73 closed to achieve the minimum volume required by the analyzers 20. In other words, even if the engine 22 is in the OFF state but a predetermined amount of time has passed since the start of the test phase, the controller 18 may close the bypass valves 57, 73 and may open the valves 58, 78 to allow the sample bags 40 to be filled with diluent gas flowing through the dilution tunnel 12 and to allow the sample bags 70 to be filled with diluent gas.

Additionally or alternatively, the controller 18 may maintain the pump 54 in the energized state and may maintain the valves 48, 50, 52 and the bypass valve 57 in the open state, and may open the valves 66, 68 and energize the pump 64 to cause fill gas 60 to enter the sample bags 40. Accordingly, the sample bags 40 may be filled with fill gas 60 during the test phase. While the controller 18 is described as filling the sample bags 40 with diluent gas from the dilution tunnel 12 or with fill gas 60, the controller 18 could fill the sample bags 40 with both diluent gas from the dilution tunnel 12 and with fill gas 60. Again, the controller 18 may at least partially fill the sample bags 40 with diluent gas from the dilution tunnel 12 or with fill gas 60 to allow the sample bags 40 to achieve a minimum volume required by the analyzers 20 to analyze the contents within the sample bags 40. The minimum sample volume required by the analyzers 20 may be predetermined by properties of the analyzers 20 such as the flow rate of the analyzers 20 as well as by the required analysis time. In sum, the controller 18 may provide the sample bags 40 with either or both of diluent gas from the dilution tunnel 12 or fill gas 60 during the test phase.

Adding diluent gas from the dilution tunnel 12 and/or fill gas 60 to the sample bags 40 during the test phase increases the efficiency of the exhaust sampling system 10, as such diluent gas and/or fill gas 60 is not added prior to or following the test phase. Accordingly, adding the diluent gas from the dilution tunnel 12 and/or fill gas 60 during the test phase streamlines the overall test, as the gas added to the sample bags 40 is added during the test phase and is not required as an additional step either prior to or following the test phase.

At the beginning of the test phase, the controller 18 determines a sample extraction rate for the sample probes 42, 44, 46 based on the volume of the sample bags 40, and the prescribed collection time (i.e., the length of the test phase). The extraction rate determined by the controller 18 at the start of the test phase may be the initial extraction rate and may be limited by the length of the test phase. For example, the sample bags 40 include a fixed or maximum volume. Accordingly, longer test phases require the controller 18 to select an extraction flow rate that, when integrated, will not exceed the volume of the sample bags 40.

During operation, the controller 18 may adjust the extraction rate of the probes 42, 44, 46 based on operation of the engine 22. Namely, the controller 18 may continuously calculate the extraction rate required to provide the sample bags 40 with a desired volume based on the time during the test phase in which the engine 22 is moved to the ON state. When the engine 22 is first moved into the ON state, the extraction flow rate is selected and is maintained until the end of the test phase to ensure proportional sampling, which is required by the proportional sampling theory of CVS and BMD systems for accurately calculating the pollutant mass contained within the diluted exhaust gas sample.

Based on the foregoing, the controller 18 may optimize the initial extraction rate by continuously calculating the extraction rate until the engine 22 is moved to the ON state, as identified by the sensor 92. Accordingly, the controller 18 ensures that the maximum extraction flow is selected, thereby allowing the controller 18 to achieve a sufficient volume of diluted exhaust gas required by the analyzers 20 during periods when the engine 22 is in the ON state.

Adjusting the extraction flow rate likewise minimizes the need for the controller 18 to supply the sample bags 40 with diluent gas from the dilution tunnel 12 and/or with fill gas 60 to provide the analyzers 20 with the minimum volume required. The controller 18 may continuously calculate and optimize the extraction flow rate of the sample probes 42, 44, 46—prior to the engine 22 moving into the ON state—to adjust the extraction flow rate such that a sufficient sample is taken when the engine 22 is in the ON state, thereby minimizing or eliminating the need to fill the sample bags 40 with diluent gas from the dilution tunnel 12 or with fill gas 60 when the engine 22 is in the OFF state. Accordingly, the sample bags 40 are filled primarily with diluted exhaust gas from the dilution tunnel 12 and, as a result, the dilution ratio of the sample contained within the sample bags 40 is minimized.

The controller 18 may achieve the extraction flow rate by controlling one or more of the valves 48, 50, 52. For example, if the sample probes 42, 44, 46 include different sized nozzles such that the first sample probe 42 provides an extraction flow rate of approximately two (2) lpm (liters per minute), the second sample probe 44 provides an extraction flow rate of approximately five (5) lpm, and the third sample probe 46 provides an extraction flow rate of approximately five (5) lpm, the controller 18 may only open the valves 48, 50 associated with the first sample probe 42 and the second sample probe 44 if the calculated extraction flow rate is approximately seven (7) lpm. Because the first sample probe 42 includes an extraction sample rate of approximately two (2) lpm and the second sample probe 44 supplies an extraction flow rate of approximately five (5) lpm, use of the first sample probe 42 and the second sample probe 44 provides a total sample extraction flow rate of approximately seven (7) lpm.

If, on the other hand, the controller 18 determines that a higher sample extraction flow rate is required (i.e., if the engine 22 is moved to the ON state later during the test phase) such that a sample extraction flow rate of approximately twelve (12) lpm is required, the controller 18 may open each of the valve 48, 50, 52 to allow the extraction flow rate provided by the sample probes 42, 44, 46 to equal approximately twelve (12) lpm (i.e., two (2) lpm from sample probe 42; five (5) lpm from sample probe 44; and five (5) lpm from sample probe 46).

The foregoing example illustrates how the controller 18 may adjust the sample extraction flow rate by controlling the valves 48, 50, 52 and only permitting flow through selective ones of the sample probes 42, 44, 46 when the engine 22 is moved to the ON state. Regardless of how the sample extraction flow rate is achieved, once the controller 18 determines the sample extraction rate, the sample extraction rate is maintained throughout the test phase and is determined based on when the engine 22 is moved into the ON state during the test phase. If pulse width modulation (PWM) is used to control one or more of the valves 42, 44, 46, proportional sampling is maintained with the flow meter 56 functioning as a feedback element.

The analyzers 20 may determine the pollutant mass (m) over the test phase based on the pollutant concentration of the proportionally collected exhaust sample and the respective integrated CVS volume. See Equation 1 below.

$$m = V_{mix} * \rho_{[pollutant]} * c * x$$

In the foregoing equation, m represents the pollutant mass in grams over the test phase; $V_{mix}$ represents the total dilute exhaust volume over the test phase at standard reference conditions (scf or $m^3$); $\rho$[pollutant] represents the density of the appropriate chemical species (g/scfm or gram/$m^3$); x represents the measured pollutant concentration in the sample after dry-to-wet and background corrections (ppmV or percent); and c represents ten-two for pollutant concentrations percentage and ten-six for pollutant concentrations in ppm.

Based on the foregoing, integration of the CVS flow rate to determine the CVS volume must be started and stopped in conjunction with filling of the sample bags 40, 70. Accordingly, the controller 18 may start and stop integration of the CVS flow rate to determine the CVS volume in Equation 1 in conjunction with starting and stopping of bag filling (i.e., filling of the sample bags 40, 70).

The controller 18 may likewise sequence filling of the sample bags 70 associated with the background collection unit 16 with filling of the sample bags 40 associated with the exhaust collection unit 14. Accordingly, when the controller 18 opens the valves 58 or provides the sample bags 40 with diluent gas and/or fill gas 60, the controller 18 likewise may open valves 78 to fill the sample bags 70 with diluent gas. In short, the sample bags 70 may be filled at the same time as the sample bags 40 such that the sample bags 70 are controlled in the same manner as the sample bags 40.

While the sample bags 70 are described as being controlled in the same manner as the sample bags 40 such that the sample bags 70 are filled with diluent gas at the same time the sample bags 40 are filled with diluted exhaust gas, diluent gas, or fill gas 60, the sample bags 70 could be controlled in a different manner. Namely, the sample bags 70 may collect diluent gas during the entire test phase. Alternatively, the volume of the collected diluent gas within the sample bags 70 may be adjusted with clean gas in a similar manner as the fill gas 60 is supplied to the sample bags 40 to ensure that the volume contained within the sample bags 70 achieves a minimum volume required for analysis by the analyzers 20.

In sum, the controller 18 controls the exhaust sampling system 10 to achieve a desired (i.e., low) dilution ratio by starting and stopping filling of the sample bags 40 with diluted exhaust gas in conjunction with engine ON/OFF times. Further, the controller 18 achieves a target volume within the sample bags 40 by selectively adding diluent gas from the dilution tunnel 12 and/or fill gas 60 to the sample bags 40 during the test phase. The controller 18 may also select the extraction flow rate achieved by the sample probes 42, 44, 46 and may continually adjust the extraction sample rate during the test phase until the engine 22 is moved to the ON state. Finally, the controller 18 may control the flow of diluent gas into the sample bags 70 such that diluent gas is received by the sample bags 70 at the same time that diluted exhaust gas, diluent gas, or fill gas 60 is received by the sample bags 40.

As described above, the controller 18 may control the exhaust sampling system 10 such that the sample bags 40 are selectively filled with diluent gas from the dilution tunnel 12 and/or fill gas 60 if the volume of diluted exhaust gas received by the sample bags 40 is insufficient to allow the analyzers 20 to properly analyze the contents of the sample bags 40. The foregoing system 10 may be simplified by removing the source of fill gas 60 such that the controller 18 only fills the sample bags 40 with diluent gas from the dilution tunnel 12 should the sample bags 40 receive an insufficient volume of diluted exhaust gas during a test phase.

Figure 2:
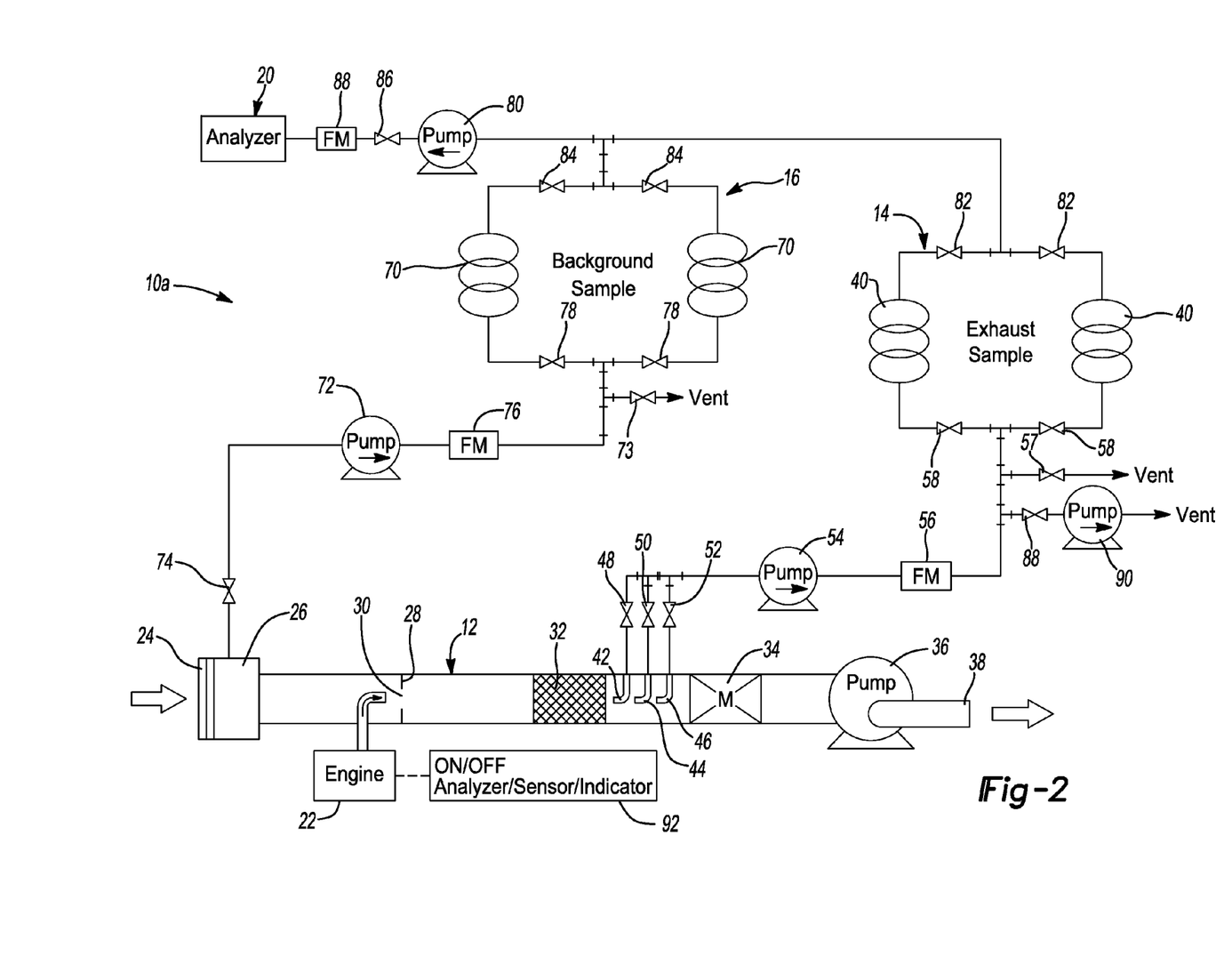
FIG. 2 is a schematic view of a CVS sampling system in accordance with the principles of the present disclosure.

A schematic representation of an exhaust sampling system 10a having the source of fill gas 60 removed is shown in FIG. 2. In view of the substantial similarity in structure and function of the components associated with the exhaust sampling system 10 with respect to the exhaust sampling system 10a, like reference numerals are used to identify like components while like reference numerals containing letter extensions are used to identify those components that have been modified.

Operation of the exhaust sampling system 10a is virtually identical to the exhaust sampling system 10 with the exception that the controller 18 only supplies the sample bags 40 with diluent gas from the dilution tunnel 12 when the volume of diluted exhaust gas supplied to the sample bags 40 is insufficient to allow the analyzers 20 to properly analyze the contents of the sample bags 40. Operation of the exhaust sampling system 10a is otherwise identical to operation of the exhaust sampling system 10. Accordingly, a detailed description of the operation of the exhaust sampling system 10a is foregone.

The foregoing systems 10, 10a optimize bag filling of a CVS system to optimize the dilution ratio of the sample(s) taken, provide enough sample in the collection bags 40 for analysis, and achieve the foregoing objectives within a defined sampling phase time. The systems 10, 10a extract samples in parallel with operation of the engine 22 and supplement the volume of the collection bags 40 when a minimum sample volume required for analysis would not be achieved. The supplemented volume may be provided to the collection bags 40 during the test phase when the engine 22 is in the OFF state.

Figure 3:
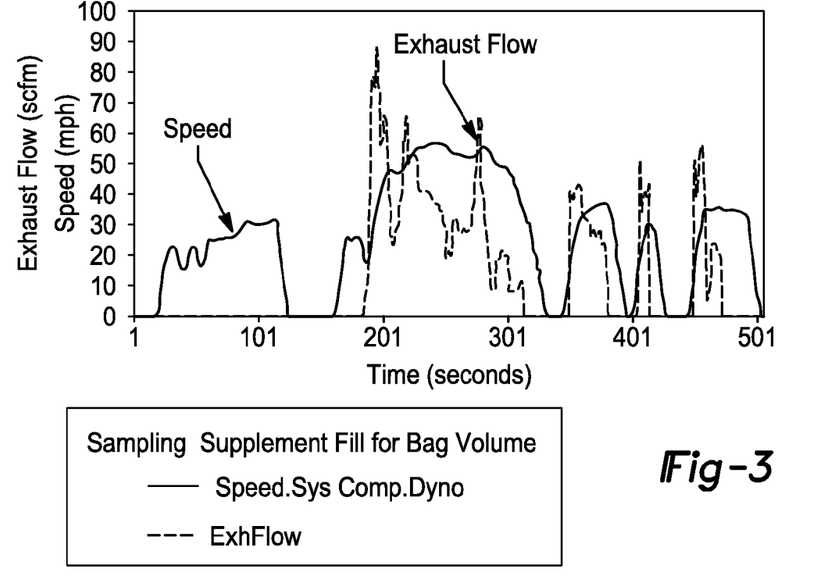
FIG. 3 is a graph of exhaust flow and vehicle speed versus time for a test cycle of an internal combustion engine.
Figure 4:
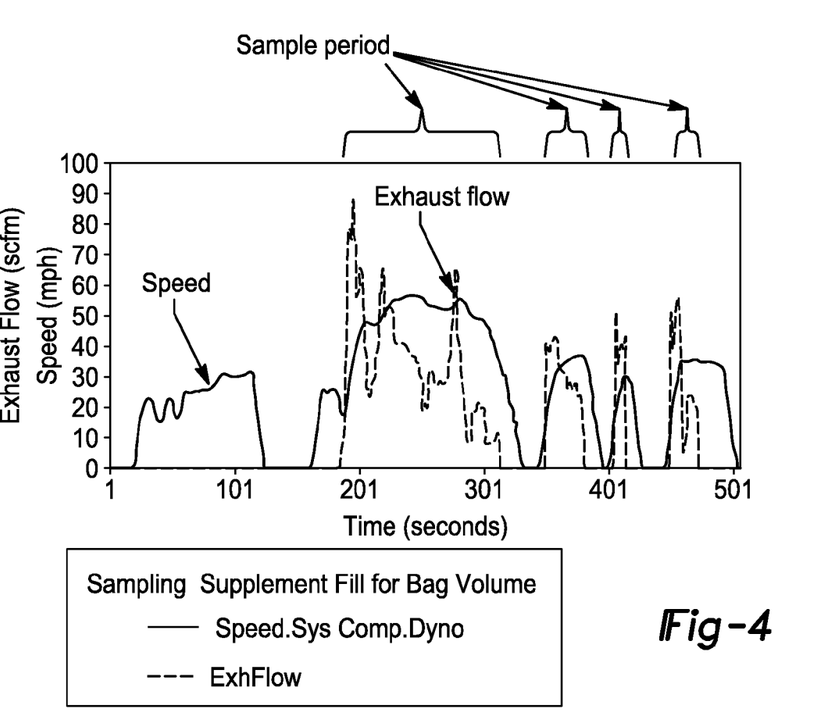
FIG. 4 is a graph of exhaust flow and vehicle speed versus time for a test cycle of an internal combustion engine that highlights when samples of the exhaust gas are taken during the test cycle.
Figure 5:
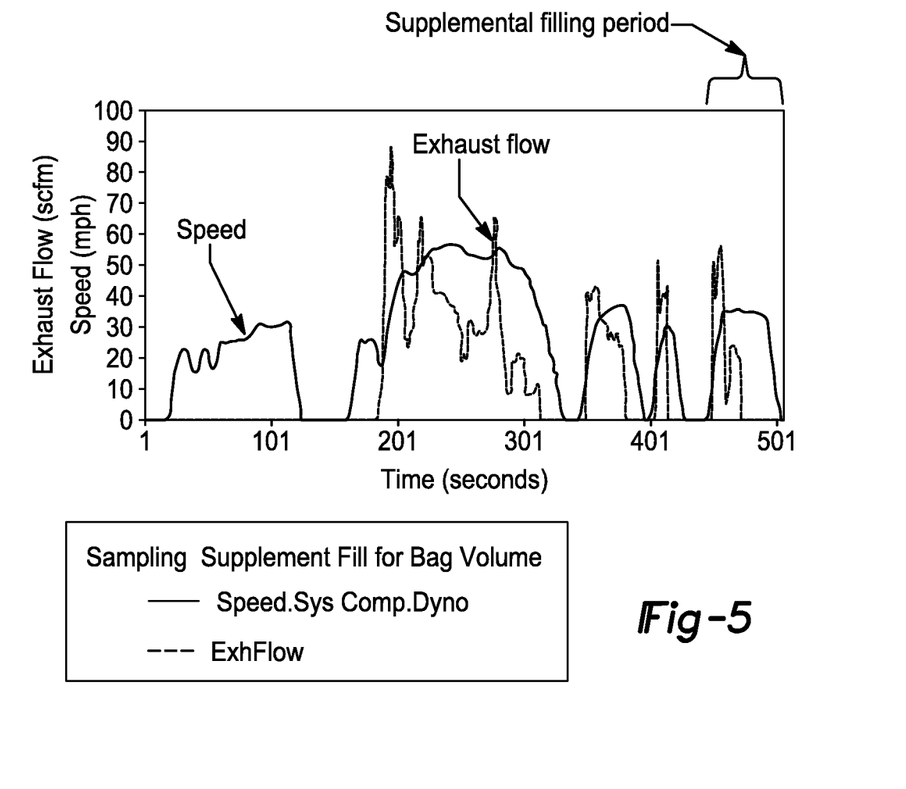
FIG. 5 is a graph of exhaust flow and vehicle speed versus time for a test cycle of an internal combustion engine that highlights a supplemental filling period performed during the test cycle.

One approach to achieve a minimum sample volume required for analysis is to integrate the bag sample volume during a test interval (i.e., test phase) and to determine the point in the test interval that sample collection is required to remain ON—for the remainder of the test interval—to achieve the minimal sample volume necessary for analysis. FIGS. 3-5 provide an example of the foregoing approach.

With reference to FIG. 3, a test interval for an engine 22 is provided. The test interval includes a run time of 505 seconds with the engine 22 only in the ON state for 191 seconds during the test interval.

If a CVS flow rate of 350 scfm is selected, the results shown below in Table 1 represent CVS standard operation. The overall dilution ratio is high but the system would have enough sample in the collection bag 40 for analysis.

TABLE 1

| Example | Integrated Sample Time | CVS Integrated Flow (cfm Based on 350 scfm) | Dilution Ratio | Collection Bag Volume (liters) |
|---|---|---|---|---|
| CVS Standard Operation | 505 | 2945.8 | 27.7 | 90.0 |

In the above test, sampling may be optimized by only collecting a sample when the engine 22 is in the ON state. Namely, CVS bag sampling is only performed during the times of the test interval that the engine 22 is in the ON state and, as a result, the system would only collect a bag sample for 191 seconds, as shown below in Table 2. The sample periods for optimized bag sampling (i.e., only sampling when the engine 22 is in the ON state) are shown in FIG. 4.

TABLE 2

| Example | Integrated Sample Time | CVS Integrated Flow (cfm Based on 350 scfm) | Dilution Ratio | Collection Bag Volume (liters) |
|---|---|---|---|---|
| CVS Standard Operation | 505 | 2945.8 | 27.7 | 90.0 |
| Optimized Bag Sampling | 191 | 1114.17 | 10.48 | 34.0 |

While the dilution ratio of the sample is improved by only extracting a sample during periods when the engine 22 is in the ON state, the collected volume often does not yield a sufficient sample required for analysis.

As described above, the collection bag 40 may be filled at some point during the test interval when the engine is in the OFF state. In FIG. 5, this period is shown at the end of the test interval. Namely, if a target sample volume is established in order to have enough sample to analyze, the control system—based on the amount of exhaust gas already collected—can recognize the point in time during the test interval when sampling will have to be turned on for the remainder of the test interval in order to collect the desired volume by the end of the test interval.

As shown below in Table 3, by filling the collection bag 40 with additional sample during the test interval when the engine 22 is in the OFF state, the sample volume for analysis is increased from 34 liters to 41.5 liters. At the same time, the dilution ratio is maintained at the lowest possible ratio consistent with obtaining enough sample to analyze.

TABLE 3

| Example | Integrated Sample Time | CVS Integrated Flow (cfm Based on 350 scfm) | Dilution Ratio | Collection Bag Volume (liters) |
|---|---|---|---|---|
| CVS Standard Operation | 505 | 2945.8 | 27.7 | 90.0 |
| Optimized Bag Sampling | 191 | 1114.17 | 10.48 | 34.0 |
| Optimized Bag Sampling With Supplemental Bag Filling | 233 | 1359.17 | 12.79 | 41.5 |

Employing optimized bag sampling (i.e., only sampling when the engine 22 is in the ON state) and providing supplemental bag filling at a selected time during the test interval when the engine 22 is in the OFF state allows the CVS system to achieve a minimum volume required for analysis and allows the CVS system to optimize dilution ratio while concurrently maintaining the minimum dilution ratio and bag volume necessary for analysis. Further, supplementing bag fill during the test interval avoids implementation of pre-dilution or post-dilution procedures (i.e., supplementing bag fill prior to or following the test interval).

Finally, existing CVS systems may be upgraded to perform the foregoing procedure without additional hardware.

Figure 6:
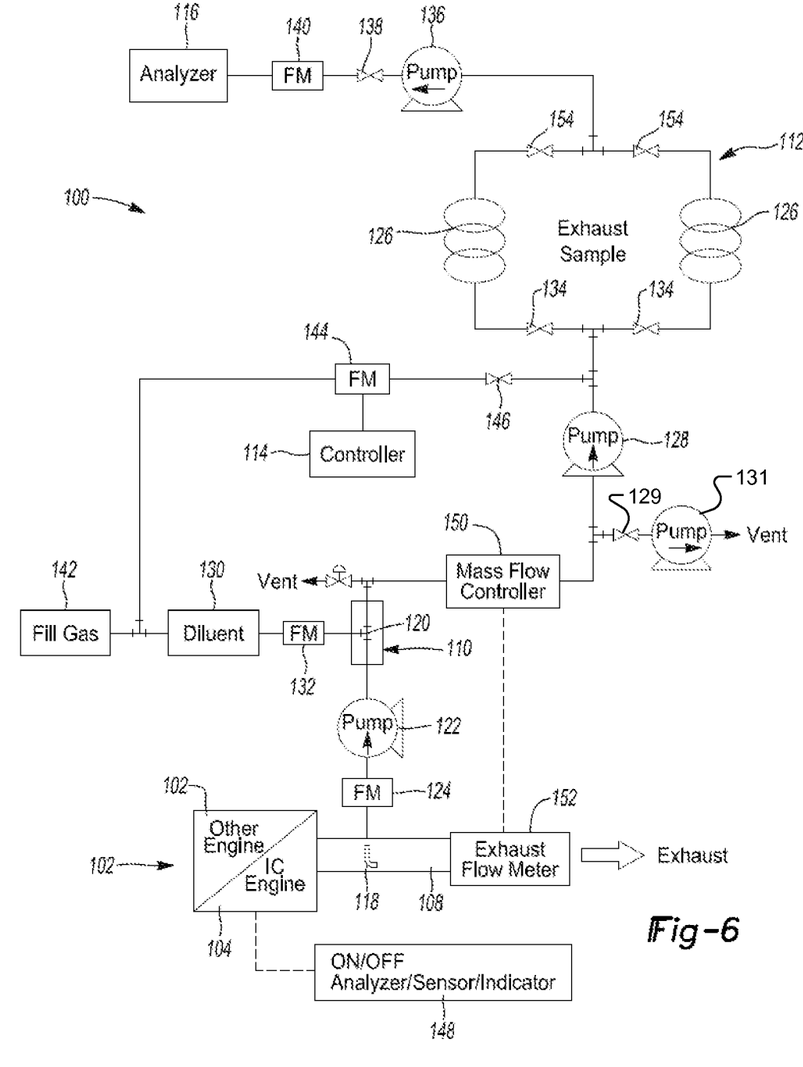
FIG. 6 is a schematic view of a BMD sampling system in accordance with the principles of the present disclosure.

With particular reference to FIG. 6, another exhaust sampling system 100 is provided. The exhaust sampling system 100 provides a BMD sampling system, whereby an exhaust sample is diluted at a fixed dilution ratio and is collected in proportion to an exhaust flow from an engine 102. In the schematic shown in FIG. 6, the engine 102 includes an internal combustion engine 104 and another engine 106 such as an electric motor that cooperate to provide a propulsion unit for a hybrid vehicle (not shown). The engine 106 may be the primary propulsion unit of the vehicle and, as a result, there may be periods of operation of the vehicle when the internal combustion engine 104 expels little or no exhaust through a tailpipe 108 of the engine 104.

The exhaust sampling system 100 may include a sampling unit 110, an exhaust collection unit 112, a controller 114, and an analyzer 116. The sampling unit 110 may be in fluid communication with a sample probe 118 and may include a mixer 120. The sample probe 118 may be received within the tailpipe 108 to allow the sample probe 118 to collect a sample of exhaust gas from the engine 102. The sample of exhaust gas may be drawn into the sampling unit 110 by a pump 122 and may be measured by a flow meter 124 disposed between the sample probe 118 and the pump 122.

The exhaust collection unit 112 may be in fluid communication with the sampling unit 110 and may include one or more sample bags 126 and a pump 128 that draws a sample of diluted exhaust gas into the sample bags 126. The diluted exhaust gas may be drawn from the sampling unit 110, where the exhaust gas received from the sample probe 118 is mixed with a diluent gas 130. Specifically, the diluent gas 130 may flow through a flow meter 132 and may subsequently be received by the mixer 120 of the sampling unit 110. The mixer 120 may mix the diluent gas 130 with the exhaust gas sample received from the sample probe 118 to create a sample of diluted exhaust gas. The diluted exhaust gas may be drawn from the sampling unit 110 by the pump 128 and may be collected by the sample bags 126 of the exhaust collection unit 112. Collection of the diluted exhaust gas by the sample bags 126 may be controlled by a pair of control valves 134 respectively associated with each of the sample bags 126.

The analyzer 116 may receive a sample of diluted exhaust gas from the sample bags 126 for analysis. Specifically, a pump 136 may draw a sample of diluted exhaust gas from the sample bags 126 and may pump the diluted exhaust gas sample through a control valve 138 and a flow meter 140 prior to the diluted exhaust gas sample reaching the analyzer 116. The analyzer 116 may analyze the diluted exhaust gas to determine the pollutant mass contained within the exhaust gas.

As with the exhaust sampling systems 10, 10a, the sample bags 126 must include a sufficient volume to allow the analyzer 116 to properly analyze the diluted exhaust gas sample. If the diluted exhaust gas sample received from the sampling unit 110 is insufficient to fill the sample bags 126, fill gas 142 may be provided to one or more of the sample bags 126 via a flow meter 144 and control valve 146.

With continued reference to FIG. 6, operation of the exhaust sampling system 100 will be described in detail. As with the exhaust sampling systems 10, 10a, any number of tests may be performed using the exhaust sampling system 100 and, further, any of the tests may include test intervals or test phases having virtually any duration. While the exhaust sampling system 10 may be used in conjunction with numerous tests and in conjunction with test intervals or test phases of virtually any length, an exemplary test phase of five hundred and five seconds (505 s) will be described hereinafter.

The controller 114 may be in communication with a sensor 148 or 152 that identifies the state of the engine 102. Namely, the sensor 148 identifies whether the engine 102 is in an ON state or an OFF state. If sensor 152 is used, the sensor 152 measures the ON or OFF state by measuring the exhaust flow. Regardless of the state of the engine 102, the controller 114 instructs the pump 122 into an energized state to draw an exhaust gas sample into the sampling unit 110 via the sample probe 118. The exhaust gas sample may be mixed with the diluent gas 130 by the mixer 120 to produce a sample of diluted exhaust gas. A mass flow controller 150 may be in communication with an exhaust flow meter 152 and may control an amount of diluted exhaust gas supplied to the sample bags 126. If the engine 102 is in the ON state, the diluted exhaust gas is received within the collection bags 126 due to the controller 114 opening the valves 134. If, on the other hand, the engine 102 is in the OFF state, the controller 114 may close the valves 134 and open a bypass valve 129. The controller 114 may also energize a pump 131 located downstream of the valve 129 to vent the diluted exhaust gas.

As with the exhaust sampling systems 10, 10a, if the volume of diluted exhaust gas supplied to the sample bags 126 is insufficient to achieve the minimum volume required, fill gas 142 may be added to the sample bags 126 during the test interval or test phase. Adding fill gas 142 to the sample bags 126 during the test interval or test phase increases the efficiency of the exhaust sampling system 100, as additional procedures either before the test phase or after the test phase are not required. Specifically, adding fill gas 142 to the sampling bags 126 prior to or following the test phase is not required, as the fill gas 142 is added during the test phase.

Once the sample bags 126 are filled with a sufficient volume of diluted exhaust gas, control valves 154 associated with the exhaust collection unit 112 may be opened to permit the analyzer 116 to receive a sample of diluted exhaust gas for analysis.

While the controller 114 is not shown in communication with each component of the exhaust sampling system 100, the controller 114 may be in communication with the sensor 148; the pumps 122, 128, 136; the control valves 138, 146, 154; the flow meters 124, 132, 140, 144, 152; and the mass flow controller 150. Accordingly, the controller 114 may control the pumps 122, 128, 136 and control valves 138, 146, 154 based on information received from the sensor 148 and the various flow meters 124, 132, 140, 144, 152.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An exhaust sampling system for an engine, the exhaust sampling system comprising:
   a dilution tunnel in which exhaust gas from the engine is diluted with a first diluent gas;
   an exhaust collection unit including at least one collection bag that selectively receives said diluted exhaust gas;

a first sample probe in fluid communication with said dilution tunnel and operable to selectively supply said at least one collection bag with a portion of said diluted exhaust gas during a test phase; and a controller operable to permit flow of said diluted exhaust gas from said first sample probe to said at least one collection bag in a first state and operable to prevent flow of said diluted exhaust gas from said first sample probe to said at least one collection bag in a second state, said controller selectively supplying a second diluent gas to said at least one collection bag during said test phase and selectively preventing flow of said second diluent gas to said at least one collection bag during said test phase.

2. The exhaust sampling system of claim 1, wherein said controller supplies said second diluent gas to said at least one collection bag based on an ON time of the engine during said test phase.

3. The exhaust sampling system of claim 2, wherein said controller supplies said second diluent gas to said at least one collection bag based on the first time during said test phase at which the engine is switched to an ON state.

4. The exhaust sampling system of claim 3, wherein said test phase has a predetermined total time period and said controller supplies said second diluent gas to said at least one collection bag based on the first point in time at which the engine is switched to an ON state during the test phase relative to said predetermined total time period of said test phase.

5. The exhaust sampling system of claim 1, further comprising a first valve associated with a first sample probe and movable between an open state permitting flow of said diluted exhaust gas to said at least one collection bag and a closed state preventing flow of said diluted exhaust gas to said at least one collection bag, said controller in communication with said first valve and operable to control movement of said first valve between said open state and said closed state.

6. The exhaust sampling system of claim 5, wherein said open state is a fully open state, said first valve being movable into one of a plurality of partially open states between said fully open state and said closed state.

7. The exhaust sampling system of claim 1, further comprising a background collection unit including at least one background sampling bag.

8. The exhaust sampling system of claim 7, wherein said background collection unit collects said first diluent gas.

9. The exhaust sampling system of claim 8, wherein said background collection unit collects said first diluent gas during said test phase.

10. The exhaust sampling system of claim 1, wherein said second diluent gas consists of said first diluent gas.

11. The exhaust sampling system of claim 10, wherein said controller allows flow of said second diluent gas to said at least one collection bag when the engine is in an ON state, and said controller selectively prevents the flow of said second diluent gas to said at least one collection bag when the engine is switched to an OFF state during said test phase.

12. The exhaust sampling system of claim 1, wherein said controller allows flow of said second diluent gas to said at least one collection bag when the engine is in an ON state, and said controller selectively prevents the flow of said second diluent gas to said at least one collection bag when the engine is switched to an OFF state during said test phase.

13. The exhaust sampling system of claim 12, wherein said controller selectively allows the flow of said second diluent gas to said at least one collection bag during said test phase when the engine is in said OFF state based on a comparison of a collected volume of said diluted exhaust gas and a desired volume.

14. The exhaust sampling system of claim 12, wherein said controller prevents the flow of said second diluent gas to said at least one collection bag during said test phase when the engine is in said OFF state during said test phase if a period that has elapsed since a start of said test phase while said engine is in said OFF state is less than a predetermined period.

15. The exhaust sampling system of claim 14, wherein said controller allows the flow of said second diluent gas to said at least one collection bag during said test phase when the engine is in said OFF state if said elapsed period is greater than or equal to said predetermined period.

16. The exhaust sampling system of claim 12, wherein said controller selectively allows the flow of said second diluent gas to said at least one collection bag during said test phase when the engine is in said OFF state.

17. An exhaust sampling system for sampling, during a test phase having a predetermined duration, the exhaust gas from an engine for a hybrid vehicle that is switched between an ON state and an OFF state over the duration of said test phase, the exhaust sampling system comprising:

a sample bag;

a diluent source configured to supply diluent for diluting said exhaust gas;

a sample probe configured to receive said diluted exhaust gas;

a first valve operable to control flow of said diluted exhaust gas from said sample probe to said sample bag; and a controller that controls said first valve to:
allow the flow of said diluted exhaust gas from said sample probe to said sample bag when the engine is in said ON state;
selectively prevent the flow of said diluent from said sample probe to said sample bag when the engine is switched to an OFF state during said test phase; and
selectively allow the flow of said diluent from said diluent source to said sample bag during the test phase when the engine is in an OFF state.

18. The exhaust sampling system of claim 17, wherein for at least a portion of said test phase, said controller is configured to control said first valve to only allow the flow of said diluent from said sample probe to said sample bag during the periods of said test phase when the engine is in said ON state.

19. The exhaust sampling system of claim 18, wherein said portion of said test phase includes the beginning of said test phase, and said controller controls said first valve to allow the flow of said diluent from said diluent source to said sample bag for the remainder of the test phase regardless of whether said engine is in said ON state or said OFF state.

20. The exhaust sampling system of claim 17, wherein said controller selectively allows flow of said diluent from said diluent source to said sample bag during said test phase when the engine is in said OFF state based on a comparison of a collected volume of said diluted exhaust gas and a desired volume.

21. The exhaust sampling system of claim 17, wherein said controller prevents flow of said diluent from said diluent source to said sample bag during said test phase when the engine is in said OFF state during said test phase if a period that has elapsed since a start of said test phase while said engine is in said OFF state is less than a predetermined period.

22. The exhaust sampling system of claim 21, wherein said controller allows flow of said diluent from said diluent source to said sample bag during said test phase when the engine is in said OFF state if said elapsed period is greater than or equal to said predetermined period.

23. The exhaust sampling system of claim 17, further comprising a dilution tunnel in which said exhaust gas is diluted with said diluent, wherein said sample probe is configured to receive a portion of said diluted exhaust gas.

24. The exhaust sampling system of claim 17, further comprising a sampling unit in which said exhaust gas is diluted with said diluent, wherein said sampling unit is disposed between said sample probe and said sample bag.

25. The exhaust sampling system of claim 17, further comprising:
 a fill gas source configured to supply fill gas to said sample bag; and
 a second valve operable to control flow of said fill gas from said fill gas source to said sample bag, wherein said controller controls said second valve to allow said fill gas to flow from said fill gas source to said sample bag independent of controlling said first valve to allow flow of said exhaust gas from said sample probe to said sample bag.

26. An exhaust sampling system for an engine, the exhaust sampling system comprising:
 a dilution tunnel in which exhaust gas from the engine is diluted with a diluent gas;
 an exhaust collection unit including at least one collection bag that selectively receives said diluted exhaust gas;
 a sample probe in fluid communication with said dilution tunnel and operable to selectively supply said at least one collection bag with a portion of said diluted exhaust gas during a test phase; and
 a controller operable to:
  allow flow of said diluted exhaust gas from said sample probe to said at least one collection bag when the engine is in an ON state during said test phase;
  selectively prevent the flow of said diluent gas from said sample probe to said at least one collection bag when the engine is in an OFF state during said test phase; and
  selectively allow the flow of said diluent gas from said sample probe to said at least one collection bag when the engine is in said OFF state during said test phase.

27. The exhaust sampling system of claim 26, wherein for at least a portion of said test phase, said controller only allows the flow of said diluent gas from said sample probe to said at least one collection bag during the periods of said test phase when the engine is in said ON state.

28. The exhaust sampling system of claim 27, wherein said controller selectively allows flow of said diluent gas from said sample probe to said at least one collection bag when the engine is in said OFF state during said test phase based on a comparison of a collected volume of said diluted exhaust gas and a desired volume.

29. The exhaust sampling system of claim 28, wherein said portion of said test phase includes the beginning of said test phase, and said controller allows the flow of said diluent gas from said sample probe to said at least one collection bag for the remainder of the test phase regardless of whether said engine is in said ON state or said OFF state.

30. The exhaust sampling system of claim 28 wherein, based on said comparison of said collected volume and said desired volume, said controller determines when to end said portion of said test phase and to start allowing the flow of said diluent gas from said sample probe to said at least one collection bag for the remainder of the test phase regardless of whether said engine is in said ON state or said OFF state.

* * * * *